(12) United States Patent
Baynham et al.

(10) Patent No.: US 11,524,163 B2
(45) Date of Patent: Dec. 13, 2022

(54) SYSTEMS AND METHODS OF PROVIDING MODULATION THERAPY WITHOUT PATIENT-PERCEPTION OF STIMULATION

(71) Applicant: Boston Scientific Neuromodulation Corporation, Valencia, CA (US)

(72) Inventors: Tamara C. Baynham, Valencia, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 712 days.

(21) Appl. No.: 16/359,191

(22) Filed: Mar. 20, 2019

(65) Prior Publication Data

US 2019/0217092 A1   Jul. 18, 2019

Related U.S. Application Data

(63) Continuation of application No. 14/338,695, filed on Jul. 23, 2014, now abandoned.

(Continued)

(51) Int. Cl.
*A61N 1/36* (2006.01)
*A61N 1/372* (2006.01)

(52) U.S. Cl.
CPC ....... *A61N 1/3615* (2013.01); *A61N 1/36071* (2013.01); *A61N 1/36139* (2013.01);
(Continued)

(58) Field of Classification Search
CPC .............. A61N 1/3615; A61N 1/36071; A61N 1/36139; A61N 1/36164; A61N 1/37241; A61N 1/36062
See application file for complete search history.

(56) References Cited

U.S. PATENT DOCUMENTS 5,938,690 A   8/1999 Law et al.
5,941,906 A   8/1999 Barreras, Sr. et al.
(Continued)

FOREIGN PATENT DOCUMENTS

AU   2014293164 B2   10/2017
CN   101557856 A    10/2009
(Continued)

OTHER PUBLICATIONS

"U.S. Appl. No. 14/338,695, Advisory Action dated Feb. 22, 2016", 6 pgs.
(Continued)

*Primary Examiner* — Eugene T Wu
(74) *Attorney, Agent, or Firm* — Schwegman Lundberg & Woessner, P.A.

(57) ABSTRACT

A neuromodulation system and method of providing sub-threshold modulation therapy. Electrical modulation energy is delivered to a target tissue site of the patient at a programmed intensity value, thereby providing therapy to a patient without perception of stimulation. In response to an event, electrical modulation energy is delivered at incrementally increasing intensity values. At least one evoked compound action potential (eCAP) is sensed in a population of neurons at the target tissue site of the patient in response to the delivery of the electrical modulation energy at the incrementally increasing intensity values. One of the incrementally increased intensity values is selected based on the sensed eCAP(s). A decreased intensity value is automatically computed as a function of the selected intensity value. Electrical modulation energy is delivered to the target tissue site of the patient at the computed intensity value, thereby providing sub-threshold therapy to the patient.

20 Claims, 5 Drawing Sheets

Related U.S. Application Data

(60) Provisional application No. 61/858,730, filed on Jul. 26, 2013.

(52) U.S. Cl.
CPC ..... *A61N 1/36164* (2013.01); *A61N 1/37241* (2013.01); *A61N 1/36062* (2017.08)

(56) References Cited

U.S. PATENT DOCUMENTS

| | | |
|---|---|---|
| 6,516,227 B1 | 2/2003 | Meadows et al. |
| 6,675,046 B2 | 1/2004 | Holsheimer |
| 6,895,280 B2 | 5/2005 | Meadows et al. |
| 6,993,384 B2 | 1/2006 | Bradley et al. |
| 7,317,948 B1 | 1/2008 | King et al. |
| 7,333,857 B2 | 2/2008 | Campbell |
| 7,539,538 B2 | 5/2009 | Parramon et al. |
| 7,650,184 B2 | 1/2010 | Walter |
| 7,869,885 B2 | 1/2011 | Begnaud et al. |
| 7,979,133 B2 | 7/2011 | Feler et al. |
| 8,019,439 B2 | 9/2011 | Kuzma et al. |
| 8,090,446 B2 | 1/2012 | Fowler et al. |
| 8,224,453 B2 | 7/2012 | De Ridder |
| 8,255,057 B2 | 8/2012 | Fang et al. |
| 8,332,047 B2 | 12/2012 | Libbus et al. |
| 8,355,797 B2 | 1/2013 | Caparso et al. |
| 8,380,318 B2 | 2/2013 | Kishawi et al. |
| 8,455,716 B2 | 6/2013 | Huang et al. |
| 8,504,147 B2 | 8/2013 | Deem et al. |
| 8,615,300 B2 | 12/2013 | Feler et al. |
| 8,649,874 B2 | 2/2014 | Alataris et al. |
| 8,676,331 B2 | 3/2014 | Parker |
| 8,731,675 B2 | 5/2014 | Ranu et al. |
| 8,751,009 B2 | 6/2014 | Wacnik |
| 9,504,838 B2 | 11/2016 | Rao et al. |
| 2003/0139781 A1 | 7/2003 | Bradley et al. |
| 2004/0116978 A1 | 6/2004 | Bradley |
| 2006/0173495 A1 | 8/2006 | Randolph et al. |
| 2007/0150036 A1 | 6/2007 | Anderson |
| 2008/0188909 A1 | 8/2008 | Bradley |
| 2009/0204173 A1 | 8/2009 | Fang et al. |
| 2010/0010566 A1 | 1/2010 | Thacker et al. |
| 2010/0121409 A1 | 5/2010 | Kothandaraman et al. |
| 2010/0249875 A1 | 9/2010 | Kishawi et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0313483 A1* | 12/2011 | Hincapie Ordonez ..................... A61N 1/36053 607/17 |
| 2012/0059446 A1 | 3/2012 | Wallace et al. |
| 2012/0083709 A1 | 4/2012 | Parker et al. |
| 2012/0253422 A1 | 10/2012 | Thacker et al. |
| 2012/0265279 A1 | 10/2012 | Zhu et al. |
| 2012/0283797 A1 | 11/2012 | De Ridder |
| 2012/0290041 A1 | 11/2012 | Kim et al. |
| 2013/0066411 A1 | 3/2013 | Thacker et al. |
| 2013/0116752 A1 | 5/2013 | Parker et al. |
| 2013/0268021 A1 | 10/2013 | Moffitt |
| 2013/0282078 A1* | 10/2013 | Wacnik ............... A61N 1/36071 607/59 |
| 2013/0296975 A1 | 11/2013 | Lee et al. |
| 2014/0081349 A1 | 3/2014 | Lee et al. |
| 2014/0236257 A1* | 8/2014 | Parker ................ A61N 1/36071 607/46 |
| 2014/0276194 A1 | 9/2014 | Osorio et al. |
| 2014/0277267 A1 | 9/2014 | Vansickle et al. |
| 2014/0277282 A1 | 9/2014 | Jaax |
| 2015/0012068 A1 | 1/2015 | Bradley et al. |
| 2015/0032181 A1 | 1/2015 | Baynham et al. |

FOREIGN PATENT DOCUMENTS

| | | |
|---|---|---|
| CN | 105407964 A | 3/2016 |
| CN | 105407964 B | 5/2018 |
| EP | 3024540 B1 | 10/2018 |
| JP | 2016525414 A | 8/2016 |
| JP | 6181307 B2 | 7/2017 |
| WO | WO-2006029257 A2 | 3/2006 |
| WO | WO-2006135791 A2 | 12/2006 |
| WO | WO-2010111358 A2 | 9/2010 |
| WO | WO-2012155188 A1 | 11/2012 |
| WO | WO-2015013398 A1 | 1/2015 |

OTHER PUBLICATIONS

"U.S. Appl. No. 14/338,695, Advisory Action dated Feb. 28, 2017", 5 pgs.
"U.S. Appl. No. 14/338,695, Appeal Brief filed Apr. 27, 2017", 29 pgs.
"U.S. Appl. No. 14/338,695, Appeal Decision dated Jan. 22, 2019", 13 pgs.
"U.S. Appl. No. 14/338,695, Applicant's Summary of Examiner Interview filed Apr. 27, 2017", 1 pg.
"U.S. Appl. No. 14/338,695, Final Office Action dated Nov. 20, 2015", 10 pgs.
"U.S. Appl. No. 14/338,695, Final Office Action dated Dec. 7, 2016", 9 pgs.
"U.S. Appl. No. 14/338,695, Non Final Office Action dated Jun. 14, 2016", 10 pgs.
"U.S. Appl. No. 14/338,695, Non Final Office Action dated Jun. 15, 2015", 16 pgs.
"U.S. Appl. No. 14/338,695, Response filed Feb. 8, 2017 to Final Office Action dated Dec. 7, 2016", 9 pgs.
"U.S. Appl. No. 14/338,695, Response filed Sep. 15, 2015 to Non Final Office Action dated Jun. 15, 2015", 12 pgs.
"U.S. Appl. No. 14/338,695, Response filed Oct. 14, 2016 to Non Final Office Action dated Jun. 14, 2016", 10 pgs.
"U.S. Appl. No. 14/338,695, Response filed Jan. 20, 2016 to Final Office Action dated Nov. 20, 2015", 15 pgs.
"European Application Serial No. 14750651.3, Response filed Sep. 8, 2016 Communication pursuant to Rules 161(1) and 162 EPC dated Mar. 4, 2016", 16 pgs.
"International Application Serial No. PCT/US2014/047804, International Preliminary Report on Patentability dated Feb. 4, 2016", 8 pgs.
"International Application Serial No. PCT/US2014/047804, International Search Report dated Sep. 23, 2014", 3 pgs.
"International Application Serial No. PCT/US2014/047804, Written Opinion dated Sep. 23, 2014", 6 pgs.
De, Ridder, et al., "Burst spinal cord stimulation for limb and back pain", World Neuro surg.doi: 101016/j.wneu.2013.01.040. Epub, (Nov. 2013), 642-649.
Perruchoud, et al., "Analgesic efficacy of high-frequency Spinal Cord Stimulation: A Randomized double-blind placebo-controlled Study", Neuromodulation Jul.-Aug. 2013;16 (4):363 -9 ; discussion 369. do i: 10.1111/ner.12027 ., (Feb. 20, 2013).
"Australian Application Serial No. 2014293164, Response filed May 15, 2017 to Examiners Report dated Jul. 19, 2016", 21 pgs.
"Canadian Application Serial No. 2,917,977, Office Action dated Oct. 17, 2016", 3 pgs.
"Chinese Application Serial No. 201480042328.8, Examiner Phone Interview dated Oct. 20, 2017", 1 pg.
"Chinese Application Serial No. 201480042328.8, Office Action dated Jul. 17, 2017", w/ English Translation, 20 pgs.
"Chinese Application Serial No. 201480042328.8, Office Action dated Nov. 2, 2016", (With English Translation), 23 pgs.
"Chinese Application Serial No. 201480042328.8, Response filed Mar. 17, 2017 to Office Action dated Nov. 2, 2016", w/ claims in English, 13 pgs.
"Chinese Application Serial No. 201480042328.8, Response filed Sep. 30, 2017 to Office Action dated Jul. 17, 2017", w/ claims in English, 17 pgs.

(56) References Cited

OTHER PUBLICATIONS

"Chinese Application Serial No. 201480042328.8, Response filed Nov. 1, 2017 to Examiner Phone Interview dated Oct. 20, 2017", w/ claims in English, 14 pgs.

"European Application Serial No. 14750651.3, Communication Pursuant to Article 94(3) EPC dated Sep. 15, 2017", 4 pgs.

"European Application Serial No. 14750651.3, Response filed Jan. 10, 2018 to Communication Pursuant to Article 94(3) EPC dated Sep. 15, 2017", 16 pgs.

"Japanese Application Serial No. 2016-529858, Office Action dated Mar. 6, 2017", w/ English translation, 8 pgs.

"Japanese Application Serial No. 2016-529858, Response filed Jun. 5, 2017 to Office Action dated Mar. 6, 2017", w/ claims in English, 7 pgs.

\* cited by examiner

SYSTEMS AND METHODS OF PROVIDING MODULATION THERAPY WITHOUT PATIENT-PERCEPTION OF STIMULATION

CLAIM OF PRIORITY

This application is a continuation of U.S. application Ser. No. 14/338,695, filed Jul. 23, 2014, which claims the benefit of priority under 35 U.S.C. § 119(e) of U.S. Provisional Patent Application Ser. No. 61/858,730, filed on Jul. 26, 2013, which is herein incorporated by reference in its entirety.

FIELD OF THE INVENTION

The present inventions relate to tissue modulation systems, and more particularly, to programmable neuromodulation systems.

BACKGROUND

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems have been applied to restore some functionality to paralyzed extremities in spinal cord injury patients.

Each of these implantable neuromodulation systems typically includes at least one neuromodulation lead implanted at the desired modulation site and an Implantable Pulse Generator (IPG) implanted remotely from the modulation site, but coupled either directly to the neuromodulation lead(s), or indirectly to the neuromodulation lead(s) via one or more lead extensions. Thus, electrical pulses can be delivered from the neuromodulator to the electrodes carried by the neuromodulation lead(s) to stimulate or activate a volume of tissue in accordance with a set of modulation parameters and provide the desired efficacious therapy to the patient. The neuromodulation system may further comprise a handheld remote control (RC) to remotely instruct the neuromodulator to generate electrical modulation pulses in accordance with selected modulation parameters. The RC may, itself, be programmed by a technician attending the patient, for example, by using a Clinician's Programmer (CP), which typically includes a general purpose computer, such as a laptop, with a programming software package installed thereon.

Electrical modulation energy may be delivered from the neuromodulation device to the electrodes in the form of an electrical pulsed waveform. Thus, electrical modulation energy may be controllably delivered to the electrodes to modulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses provided through the electrode array. Each electrode configuration, along with the electrical pulse parameters, can be referred to as a "modulation parameter set."

With some neuromodulation systems, and in particular, those with independently controlled current or voltage sources, the distribution of the current to the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulation device to generate electrical pulses in accordance with the selected modulation parameters. Typically, the modulation parameters programmed into the neuromodulation device can be adjusted by manipulating controls on the external control device to modify the electrical modulation energy delivered by the neuromodulation device system to the patient. Thus, in accordance with the modulation parameters programmed by the external control device, electrical pulses can be delivered from the neuromodulation device to the electrode(s) to modulate a volume of tissue in accordance with the set of modulation parameters and provide the desired efficacious therapy to the patient. The best modulation parameter set will typically be one that delivers electrical energy to the volume of tissue that must be modulate in order to provide the therapeutic benefit (e.g., treatment of pain), while minimizing the volume of non-target tissue that is modulated.

However, the number of electrodes available combined with the ability to generate a variety of complex electrical pulses, presents a huge selection of modulation parameter sets to the clinician or patient. For example, if the neuromodulation system to be programmed has an array of sixteen electrodes, millions of modulation parameter sets may be available for programming into the neuromodulation system. Today, neuromodulation system may have up to thirty-two electrodes, thereby exponentially increasing the number of modulation parameters sets available for programming.

To facilitate such selection, the clinician generally programs the neuromodulation device through a computerized programming system. This programming system can be a self-contained hardware/software system, or can be defined predominantly by software running on a standard personal computer (PC). The PC or custom hardware may actively control the characteristics of the electrical pulses generated by the neuromodulation device to allow the optimum modulation parameters to be determined based on patient feedback or other means and to subsequently program the neuromodulation device with the optimum modulation parameter set or sets. The computerized programming system may be operated by a clinician attending the patient in several scenarios.

For example, in order to achieve an effective result from conventional SCS, the lead or leads must be placed in a location, such that the electrical modulation (and in this case, electrical modulation) will cause paresthesia. The paresthesia induced by the electrical modulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When leads are implanted within the patient, the computerized programming system, in the context of an operating room (OR) mapping procedure, may be used to instruct the neuromodulation device to apply electrical modulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the modulation energy away from the target site. By reprogramming the neuromodulation device (typically by independently varying the modulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

Although alternative or artifactual sensations are usually tolerated relative to the sensation of pain, patients sometimes report these sensations to be uncomfortable, and therefore, they can be considered an adverse side-effect to neuromodulation therapy in some cases. Because the perception of paresthesia has been used as an indicator that the applied electrical energy is, in fact, alleviating the pain experienced by the patient, the amplitude of the applied electrical energy is generally adjusted to a level that causes the perception of paresthesia. It has been shown, however, that the delivery of sub-threshold electrical energy (e.g., high-rate pulsed electrical energy and/or low pulse width electrical energy) can be effective in providing neuromodulation therapy for chronic pain without causing paresthesia.

However, because there is a lack of paresthesia that may otherwise indicate that the activated electrodes are properly located relative to the targeted tissue site, it is difficult to immediately determine if the delivered sub-threshold neuromodulation therapy is optimized in terms of both providing efficacious therapy and minimizing energy consumption. Furthermore, if the implanted neuromodulation lead(s) migrate relative to the target tissue site to be modulated, it is possible that the sub-threshold neuromodulation may fall outside of the effective therapeutic range (either below the therapeutic range if the coupling efficiency between the neuromodulation lead(s) and target tissue site decreases, resulting in a lack of efficacious therapy, or above the therapeutic range if the coupling efficiency between the neuromodulation lead(s) and the target tissue site increases, resulting in the perception of paresthesia or inefficient energy consumption). Similarly, a change in the patient's physical activity and/or posture may also cause the neuromodulation lead(s) to migrate relative to the target tissue, and/or alternatively impede optimal treatment contact to the target tissue, consequently rendering the sub-threshold neuromodulation therapy inefficacious.

There, thus, remains a need to provide a neuromodulation system that is capable of compensating for the migration of neuromodulation lead(s) and/or a change in physical activity and/or posture during sub-threshold neuromodulation therapy.

SUMMARY OF THE INVENTION

In accordance with a first aspect of the present inventions, a method of providing therapy to a patient is provided. The method comprises delivering electrical modulation energy to a target tissue site of the patient at a programmed intensity value (e.g., an amplitude value or a pulse width value), thereby providing therapy to the patient without the perception of paresthesia, delivering, in response to an event, electrical modulation energy at a series of incrementally increasing intensity values relative to the programmed intensity value, sensing at least one evoked compound action potential (eCAP) in a population of neurons at the target tissue site of the patient in response to the delivery of the electrical modulation energy at the series of incrementally increasing intensity values of the electrical modulation energy, selecting one of the series of incrementally increased intensity values based on the at least one sensed eCAP, automatically computing a decreased intensity value as a function of the selected intensity value and delivering electrical modulation energy to the target tissue site of the patient at the computed intensity value.

In one method, the selected intensity value may correspond to the intensity value of the delivered electrical modulation energy in response to which a first one of the at least eCAP is sensed.

The method may also include comparing a characteristic of each of the at least one sensed eCAP to a corresponding characteristic of a reference eCAP that is indicative of a perception threshold and selecting one of the series of incrementally increased intensity values based on the comparison. The characteristic of the each sensed eCAP may be at least one a peak delay, width, amplitude and waveform morphology.

When the sensed eCAP comprises two or more eCAPs respectively sensed in response to the delivery of the electrical modulation energy at two or more of the intensity values, the method may also include obtaining the characteristic from a stored reference eCAP, determining one of the two or more sensed eCAPs having the characteristic that best matches the characteristic of the reference eCAP.

The characteristic of the reference eCAP may be a stored threshold value. When the at least one sensed eCAP comprises one or more eCAPs respectively sensed in response to the delivery of the electrical modulation energy at each of two or more of the intensity values, the method may also comprise determining a function of the one or more sensed eCAPs having the characteristic that equals or exceeds the threshold value.

The method may also include storing a list of reference eCAPs characteristics, each of which is indicative of a perception threshold when the patient is engaged in a particular physical activity and/or posture, identifying a physical activity and/or posture in which the patient is currently engaged, and selecting, from the list of reference eCAP characteristics, the reference eCAP characteristic corresponding to the identified physical activity and/or posture, and comparing the characteristic of each of the at least one sensed eCAP to the selected reference eCAP.

The event may be an identified physical activity and/or posture, a user-initiated signal, a signal indicating migration of an electrode from which the electrical modulation energy is delivered, and a predetermined periodically recurring signal. The user-initiated signal may be generated by an external control device in some methods.

The computed function may be percentage of the selected intensity value. The percentage may be in the range of 10%-90%, 40%-60%, or 30%-70%. In another method, the computed function may be a difference between the selected intensity value and a constant.

In accordance with a second aspect of the present inventions, a neuromodulation system for use with a patient is provided. The neuromodulation system comprises a plurality of electrical terminals configured to be respectively coupled to a plurality of electrodes implanted within a target tissue site, modulation output circuitry coupled to the plurality of electrical terminals to deliver electrical modulation energy to the target tissue site of the patient at a programmed intensity value, thereby providing therapy to the patient without the perception of paresthesia, monitoring circuitry coupled to the plurality of electrical terminals, control/processing circuitry configured to direct, in response to an event, the modulation output circuitry to deliver electrical modulation energy at a series of incrementally increasing intensity values relative to the programmed intensity value, prompt the modulation output circuitry to evoke at least one compound action potential (CAP) in a population of neurons in the target tissue site of the patient in response to the delivery of the electrical modulation energy at the series of incrementally increased intensity values, prompt the monitoring circuitry to sense the at least one evoked CAP (eCAP), select one of the series of incrementally increased intensity values based on the at least one sensed eCAP, automatically compute a decreased value as a function of the selected intensity value, and direct the modulation output circuitry to deliver electrical modulation energy to the target tissue site of the patient at the computed intensity value.

In one embodiment, the selected intensity value corresponds to the intensity value of the delivered electrical modulation energy in response to which a first one of the at least one eCAP is sensed.

In another embodiment, the neuromodulation system further comprises a memory configured to store at least one characteristic of a reference eCAP indicative of a perception threshold. The controller/processing circuitry may be further configured to compare a characteristic of each of the at least one sensed eCAP to a corresponding characteristic of a reference eCAP, and select one of the series of incrementally increased intensity values based on the comparison. The characteristic of the each sensed eCAP may be at least one a peak delay, width, amplitude and waveform morphology.

When the sensed eCAP comprises two or more eCAPs respectively sensed in response to the delivery of the electrical modulation energy at two or more of the intensity values, the control/processing circuitry may be further configured to obtain the characteristic from a stored reference eCAP, determine one of the two or more sensed eCAPs having the characteristic that best matches the characteristic of the reference eCAP, and select the intensity value of the delivered electrical modulation energy in response to which the determined eCAP is sensed.

When the at least one sensed eCAP comprises one or more eCAPs respectively sensed in response to the delivery of the electrical modulation energy at each of two or more of the intensity values, the control/processing circuitry may be further configured to determine a function of the one or more sensed eCAPs having the characteristic that equals or exceeds the threshold value and select the intensity value of the delivered electrical modulation energy in response to which the determined one or more eCAPs is sensed.

In another embodiment, the memory may be further configured to store a list of reference eCAP characteristics, each of which is indicative of a perception threshold when the patient is engaged in a particular physical activity and/or posture. The control/processing circuitry may be further configured to identify a physical activity and/or posture in which the patient is currently engaged, and select, from the list of reference eCAP characteristics, the reference eCAP characteristic corresponding to the identified physical activity and/or posture, and compare the characteristic of each of the at least one sensed eCAP to the selected reference eCAP.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord modulation (SCM) system. However, it is to be understood that the while the invention lends itself well to applications in SCM, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
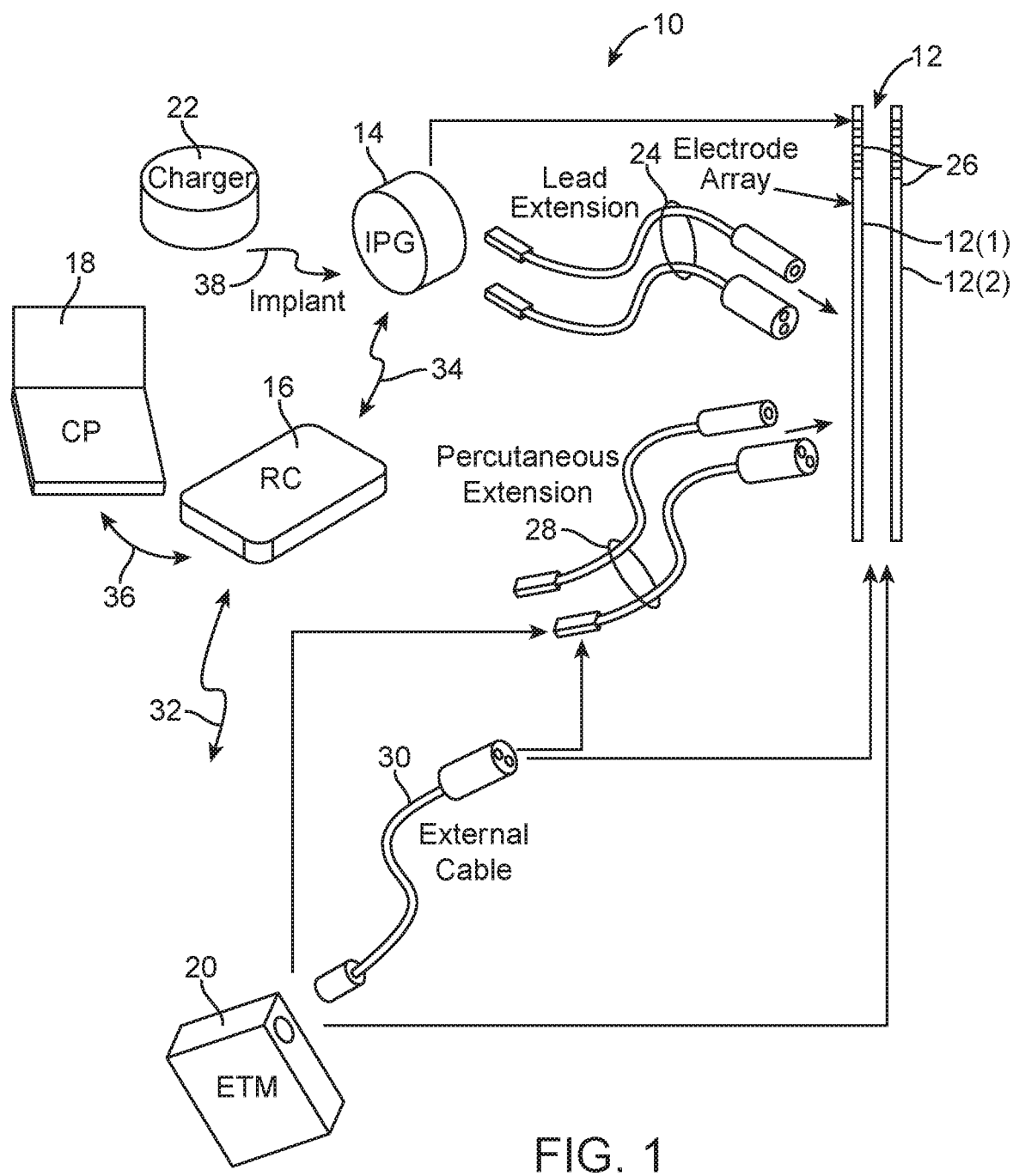
FIG. 1 is a plan view of a Spinal Cord Modulation (SCM) system constructed in accordance with one embodiment of the present inventions.

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead in can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20. For purposes of brevity, the details of the ETM 20 will not be described herein.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38.

Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

Figure 2:
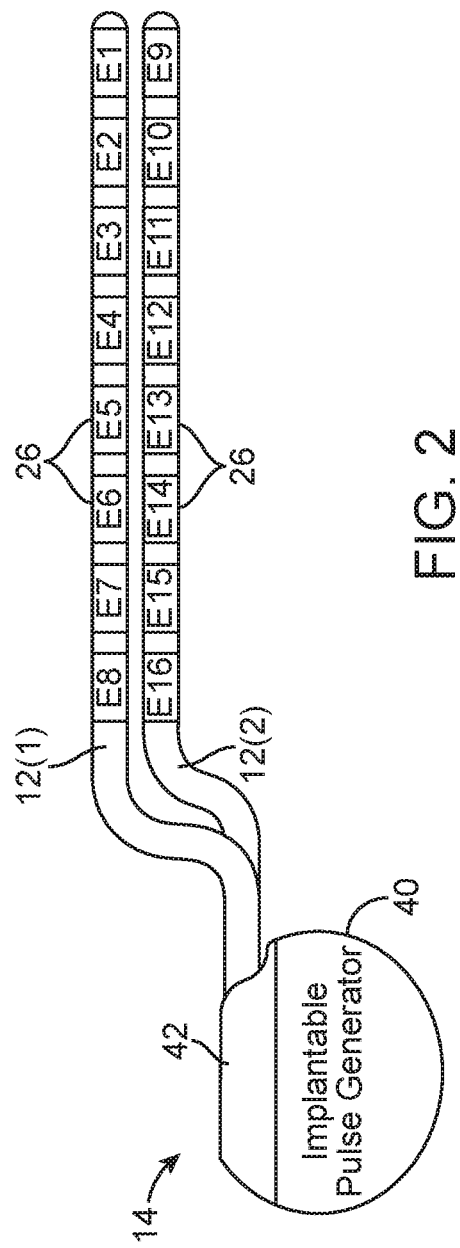
FIG. 2 is a profile view of an implantable pulse generator (IPG) used in the SCM system of FIG. 1.

Referring now to FIG. 2, the external features of exemplary neuromodulation leads 12 and the IPG 14 will be briefly described. One of the neuromodulation leads 12(1) has eight electrodes 26 (labeled E1-E8), and the other neuromodulation lead 12(2) has eight electrodes 26 (labeled E9-E16). Of course, the number and shape of the leads and the electrodes may vary based on the intended application of the neuromodulation system. Further details describing the construction and method of manufacturing percutaneous neuromodulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," which are expressly incorporated herein by reference. In some embodiments, a surgical paddle lead can be utilized, the details of which are disclosed in U.S. Patent Publication. No. 2007/0150036 A1, entitled "Stimulator Leads and Methods for Lead Fabrication and 2012/0059446 A1 entitled Collapsible/Expandable Tubular Electrode Leads," which is expressly incorporated herein by reference.

The IPG 14 comprises an outer case 40 for housing the electronic and other components (described in further detail below), and a connector 42 to which the proximal ends of the neuromodulation leads 12 mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a pulse generation circuitry that provides electrical modulation energy to the electrodes 26 in accordance with a set of modulation parameters. Such parameters may include electrode combinations, which define the electrodes that are activated as anodes (positive), cathodes (negative), and turned off (zero). The modulation parameters may further include pulse amplitude (measured in milliamps or volts depending on whether the IPG 14 supplies constant current or constant voltage to the electrodes), pulse width (measured in microseconds), pulse rate (measured in pulses per second), duty cycle (pulse width divided by cycle duration), burst rate (measured as the modulation energy on duration X and modulation energy off duration Y), and pulse shape.

With respect to the pulse patterns provided during operation of the system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG outer case 40. Electrical energy may be transmitted to the tissue in a monopolar or multipolar (for example, bipolar, tripolar and similar configurations) fashion or by any other means available.

The IPG 14 may be operated in either a super-threshold delivery mode or a sub-threshold delivery mode. While in the super-threshold delivery mode, the IPG 14 is configured for delivering electrical modulation energy that provides super-threshold therapy to the patient (in this case, causes the patient to perceive paresthesia). For example, an exemplary super-threshold pulse train may be delivered at a relatively high pulse amplitude (e.g., 5 ma), a relatively low pulse rate (e.g., less than 1500 Hz, preferably less than 500 Hz), and a relatively high pulse width (e.g., greater than 100 μs, preferably greater than 200 μs).

While in the sub-threshold delivery mode, the IPG 14 is configured for delivering electrical modulation energy that provides sub-threshold therapy to the patient (in this case, does not cause the patient to perceive paresthesia). For example, an exemplary sub-threshold pulse train may be delivered at a relatively low pulse amplitude (e.g., 2.5 ma), a relatively high pulse rate (e.g., greater than 1500 Hz, preferably greater than 2500 Hz), and a relatively low pulse width (e.g., less than 100 μs, preferably less than 50 μs).

Figure 3:
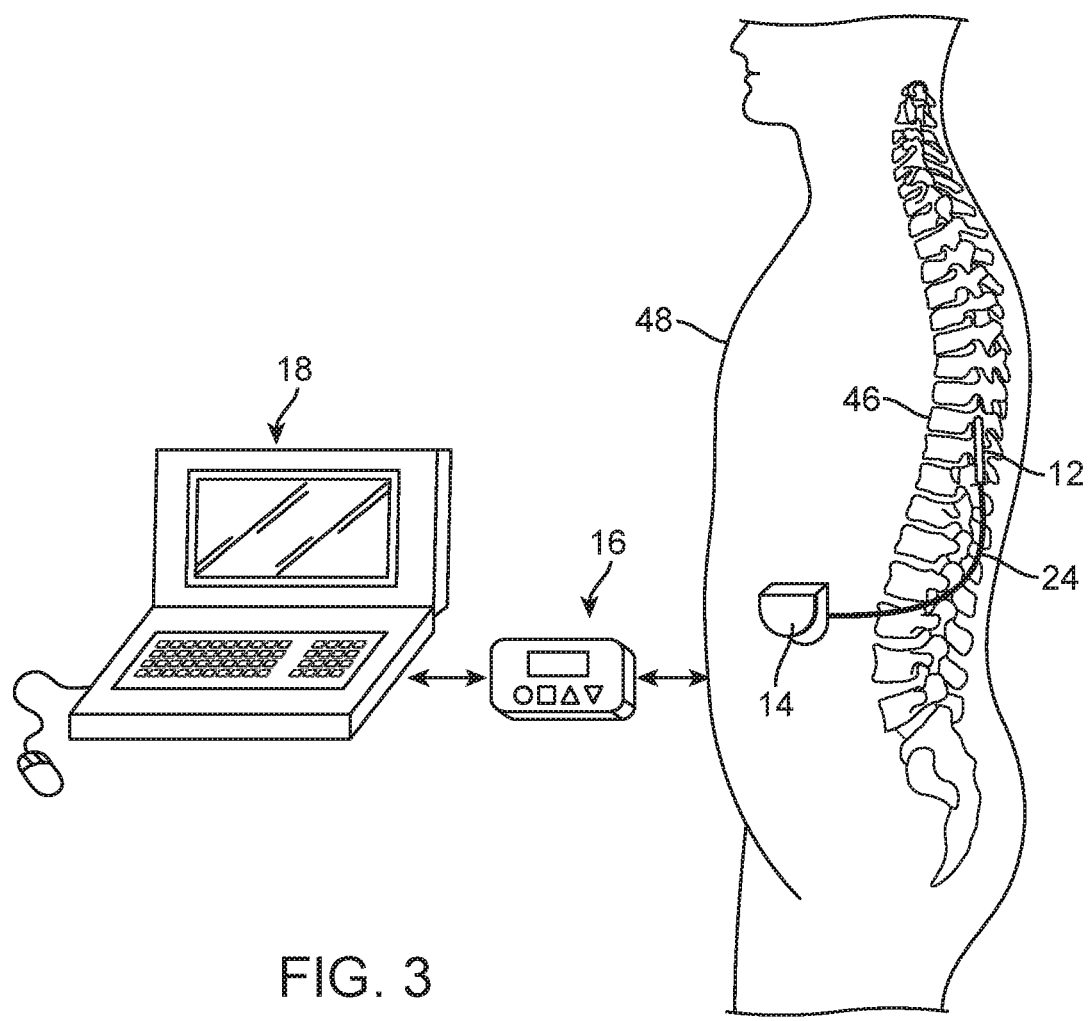
FIG. 3 is a plan view of the SCM system of FIG. 1 in use with a patient.

As shown in FIG. 3, the neuromodulation leads 12 are implanted within the spinal column 46 of a patient 48. The preferred placement of the neuromodulation leads 12 is adjacent, i.e., resting near, or upon the dura, adjacent to the spinal cord area to be stimulated. The neuromodulation leads 12 will be located in a vertebral position that depends upon the location and distribution of the chronic pain. For example, if the chronic pain is in the lower back or legs, the neuromodulation leads 12 may be located in the mid- to low-thoracic region (e.g., at the T9-12 vertebral levels). Due to the lack of space near the location where the neuromodulation leads 12 exits the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

More significant to the present inventions, because sub-threshold therapy does not produce paresthesia, it is important to continuously monitor the sub-threshold modulation energy to ensure that the patient is receiving optimal treatment. To this end, the IPG 14 is configured to automatically initiate calibration of sub-threshold therapy that may have fallen outside of the therapeutic range. The goal of the calibration process is to determine a perception threshold, and then compute a decreased intensity value as a function of the perception threshold to be used in sub-threshold modulation therapy.

In the illustrated embodiment, initiation of the calibration process may be triggered by a particular event, such as, e.g., a user actuation of a control element located on the RC 16 or CP, a sensor signal indicating that one or more of the neuromodulation leads 12 has migrated relative to a target site in the patient, a sensor signal indicating that the patient's physical activity and/or posture has changed relative to a previous physical activity and/or posture, or a periodically recurring signal generated in response to an elapsed time, a time of day, day of the week, etc.

Once the sub-threshold calibration is initiated, the SCM system 10 delivers the modulation output energy to the electrodes 26 at incrementally increasing intensity values, such as amplitude values (e.g., amplitude at a 0.1 mA step size). Preferably, if the amplitude values are incrementally increased, the other modulation parameters, such as the electrode combination, pulse rate, and pulse width are not altered during the incremental increase of the amplitude. Thus, the only modulation parameter of the sub-threshold modulation program that is altered is the pulse amplitude. In the instance in which the intensity value is pulse width (e.g., at a 10 μs step size), the only modulation parameter of the sub-threshold modulation program that is altered in pulse width.

In response to the delivered electrical modulation energy at the incrementally increasing intensity values, at least one compound action potential (CAP) is evoked by the modulation of neural tissue at the target tissue site. An evoked CAP (eCAP) is the simultaneous evoking of action potentials traveling down a population of neurons. Thus, the total magnitude of the eCAP is proportional to the number of neurons that are carrying action potentials, and therefore, may function as a clinical measurement as to the intensity level (i.e., strength of the conveyed electrical modulation energy), which is both the dose of therapy that is used to decrease the pain in the patient, and the physiological signal that causes the patient to perceive either comfortable paresthesia, painful overstimulation, or lack of stimulation. Significantly, the eCAP(s) (which in some cases, may only be one eCAP, and in other cases may be several eCAPs) are used as indicators of the perception threshold of the patient. To this end, the SCM system 10 senses and measures these eCAP(s), the characteristics of which may be used to ultimately determine a suitable intensity for sub-threshold modulation therapy, as will be described in further detail below.

To determine the perception threshold, the SCM system 10 evaluates the measured eCAP(s) and selects intensity value corresponding to at least one of the measured eCAP(s) as the perception threshold.

In one embodiment, the SCM system 10 may automatically select the amplitude value at which a first eCAP is sensed as the perception threshold. For example, when the amplitude of the delivered electrical modulation energy is incrementally increased, the first eCAP may be sensed at 5.1 mA. Thus, the SCM system 10 may select the amplitude value corresponding to 5.1 mA as the perception threshold.

Alternatively, the SCM system 10 may automatically select the amplitude value based on a comparison between the measured eCAPs and a reference eCAP indicative of the perception threshold. The reference eCAP, which may be determined empirically, captures the characteristics of an eCAP at the amplitude of the delivered electrical modulation energy at which the patient felt paresthesia (the perception threshold). This reference eCAP (or a characteristic or characteristics of the reference eCAP) may then be used to compare the eCAP(s) (or characteristics of the eCAPs) measured in response to the delivery of the electrical modulation energy during the calibration process. The characteristics of the eCAP may include, e.g., amplitude, peak delay, width, as well as waveform morphology.

For example, in one technique, the SCM system 10 may compare a waveform morphology of the measured eCAP to the waveform morphology of the reference eCAP to select the eCAP whose waveform morphology most closely resembles that of the reference eCAP. Thus, the amplitude of the delivered energy that resulted in the eCAP that most closely resembles the reference eCAP is determined to be the perception threshold.

In another technique, the SCM system 10 may store a particular characteristic of the reference eCAP as a threshold value to be used in determining the perception threshold. In this case, the SCM system 10 may compare a value of a selected characteristic of the measured eCAP to the stored threshold value. In one example, the threshold value may simply be the amplitude of the reference eCAP. In such a case, when the amplitude of a measured eCAP is equal to or greater than the threshold value, the amplitude of the delivered energy that resulted in that measured eCAP is determined to be the perception threshold. In another example, the threshold value may be the peak delay of the reference eCAP, such that when the peak delay of a measured eCAP is equal to or greater than the threshold value, the amplitude of the delivered energy that resulted in that measured eCAP is determined to be the perception threshold. In yet another example, the threshold value may be width of the reference eCAP, such that when the width of a measured eCAP is equal to or greater than the threshold value, the amplitude of the delivered energy that resulted in that measured eCAP is determined to be the perception threshold.

Although the previous examples have been focused on comparing a characteristic of a single eCAP to the reference eCAP, it should be appreciated that a function of characteristic(s) of multiple eCAP measurements may be compared to the reference eCAP. That is, because multiple eCAPs may be measured in response to the corresponding pulses in the electrical pulse train delivered at a specific amplitude value, a function (e.g., an average) of a characteristic of these eCAPs may be compared to the reference eCAP. This can be particularly useful in increasing the signal-to-noise ratio. For example, assume that an electrical pulse train comprises ten pulses in response to which ten eCAP measurements are respectively made. When the amplitude of the electrical pulse train is high enough, or close to that of the perception threshold, ten eCAPs may be measured in response to the ten pulses. Any one of these measured eCAPs will thus be truly indicative of the perception threshold. When the amplitude of the electrical pulse train is at a lower level, however, only one CAP may be evoked in response to the ten pulses and the other nine of the eCAP measurements may be zero. This one measured eCAP will thus not be indicative of the perception threshold.

To avoid such anomalies that may be caused by noise and/or system errors, an average of all the eCAP measurements at a particular amplitude value may render more accurate results than using individual eCAP measurements. It should be appreciated that the signal-to-noise ratio is reduced when a higher number of eCAP measured are used for comparison, bringing the average of the eCAP measurements closer to the true indication of whether or not the perception threshold has been reached. Thus, to increase the signal-to-noise ratio, the average of the eCAP measurements for each amplitude value of the delivered electrical pulse train may be compared to the reference eCAP. For example, if the average of all the eCAP measurements made in response to an electrical pulse train of a particular amplitude value equal or exceed the threshold value, that amplitude value is determined to be the perception threshold.

Although in the previous embodiments, only one reference eCAP is described as being stored, multiple reference eCAPs from which one reference eCAP can be selected for comparison can be stored. For example, in one embodiment, the SCM system 10 may store a list of reference eCAPs associated with a set of patient activities and/or postures. The perception threshold and corresponding reference eCAP may be different when the patient is walking as compared to when the patient is lying down, or sitting. These reference eCAPs, which are indicative of perception thresholds when the patient is engaged in a particular activity and/or posture, may be determined empirically and recorded. For example, each physical activity and/or posture may be characterized in the laboratory for each individual patient to generate a personalized look-up table that correlates the physical activity and/or posture with a reference eCAP. The SCM system 10 is configured to identify the physical activity and/or posture of the patient, as will be described below, and select the appropriate reference eCAP for comparison with the measured eCAP(s).

There may be many ways to identify the physical activity and/or posture of the patient. In one technique, the patient's physical activity and/or posture may be tracked and identified by measuring electrical parameter data (i.e., interelectrode impedance and/or measured field potentials) and performing time-varying analysis on the measured electrical parameter data, as disclosed in U.S. Patent Publication. No. 2008/0188909 A1, entitled "Neurostimulation system and method for measuring patient activity," which is expressly incorporated herein by reference. In another technique, the patient's physical activity and/or posture may be tracked and identified using an orientation sensitive device that is implanted in the IPG 14, as described in U.S. patent application Ser. No. 13/446,191, entitled "Sensing Device For Indicating Posture of a Patient Implanted With a Neurostimulation Device," which is expressly incorporated herein by reference. In still another technique, the patient's physical activity and/or posture may be tracked and identified by measuring characteristic impedance waveform morphologies, as described in U.S. Pat. No. 7,317,948, which is expressly incorporated herein by reference.

It should be appreciated that the physical activity and/or posture of the patient may be identified regardless of the nature of the event that triggers the calibration process. Thus, the calibration process may be initiated by an event independent from the identification of the physical activity and/or posture, in which case, the physical activity and/or posture is identified only to determine the reference eCAP for comparison with the measured eCAPs. However, the event itself may be identification of a triggering physical activity and/or posture, in which case, the calibration process is initiated by it in addition to helping determine the reference eCAP. For example, the SCM system 10 might detect that the patient is engaged in a triggering physical activity (e.g., running) and initiate the calibration process. In this case, the SCM system 10 is similarly configured to select the reference eCAP associated with the identified triggering physical activity and/or posture and compare the selected reference eCAP with the measured eCAP(s) to determine the perception threshold. Constantly calibrating the SCM system 10 whenever the patient changes his posture or physical activity may prove to be rather inefficient. Accordingly, the SCM system 10 may be provided with a predetermined list of triggering physical activities, such that the SCM system 10 only initiates the calibration process when a triggering physical activity and/or posture is identified. For example, only physical strenuous activities like running, lifting weights, etc., may trigger calibration.

Once the perception threshold has been determined, the SCM system 10 automatically computes a decreased amplitude for sub-threshold modulation as a function of the perception threshold. The function of the selected amplitude value is designed to ensure that the modulation energy subsequently delivered to the patient at the computed amplitude value falls within the sub-threshold therapy range. For example, the computed function may be a percentage (preferably in the range of 30%-70%, and more preferably in the range of 40%-60%) of the last incrementally increased amplitude value. As another example, the computed function may be a difference between the last incrementally increased amplitude value and a constant (e.g., 1 mA). The SCM system 10 is also configured for modifying the sub-threshold modulation program stored in the IPG 14, such that the modulation energy is delivered to the electrodes 26 in accordance with the modified modulation program at the computed amplitude value.

Figure 4:
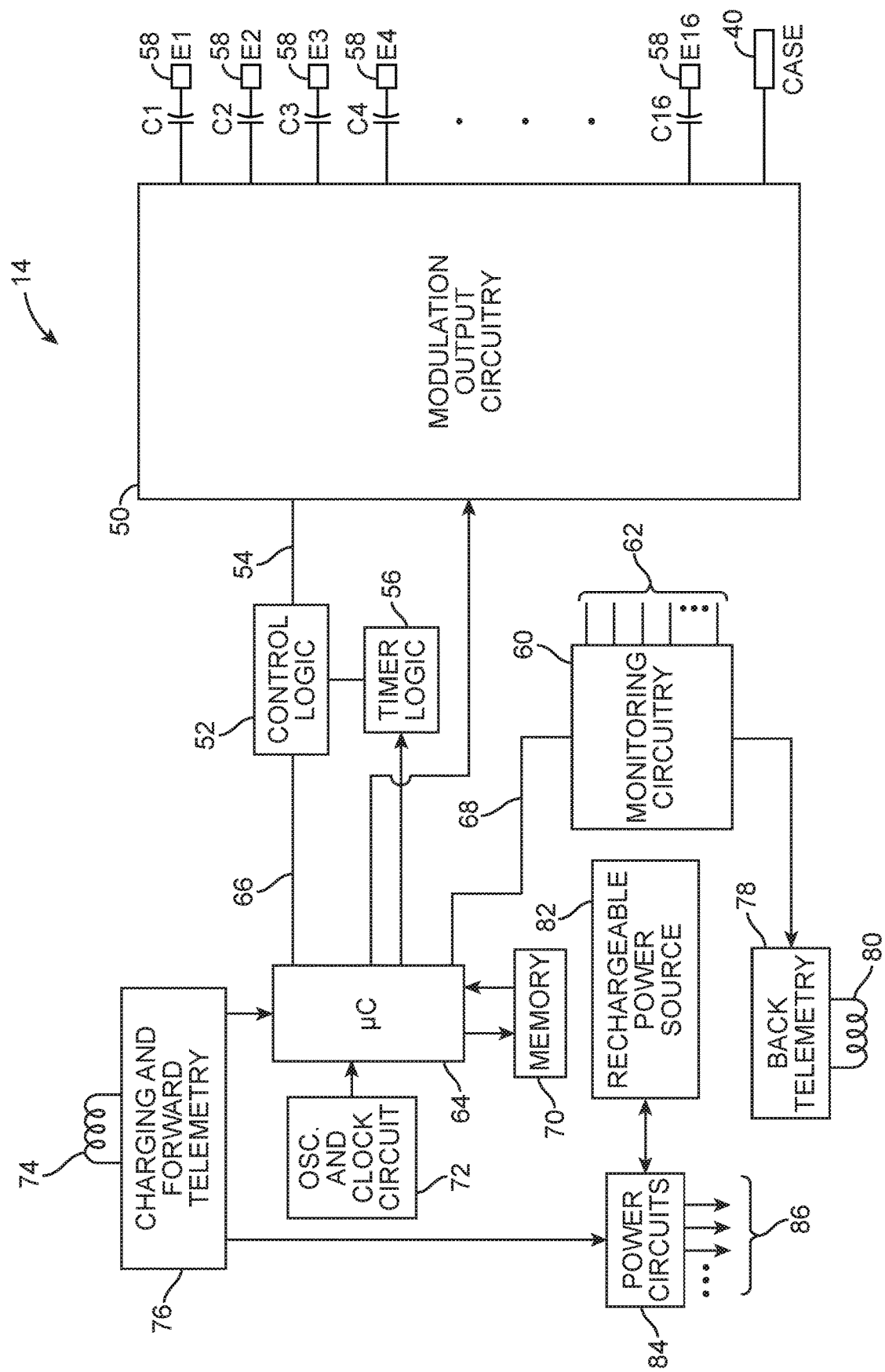
FIG. 4 is a block diagram of the internal components of the IPG of FIG. 2.

Turning next to FIG. 4, one exemplary embodiment of the IPG 14 will now be described. The IPG 14 includes modulation output circuitry 50 configured for generating electrical modulation energy in accordance with an electrical pulse train having a programmed pulse amplitude, pulse rate, pulse width, duty cycle, burst rate, and shape under control of control logic 52 over data bus 54. The pulse rate and the duration of stimulation may be controlled by analog circuitry, or digital timer logic circuitry 56 controlling the analog circuitry, and which may have a suitable resolution, e.g., 10 µs. The modulation energy generated by the modulation output circuitry 50 is output via capacitors C1-C16 to electrical terminals 58 respectively corresponding to electrodes E1-E16.

The modulation output circuitry 50 may either include independently controlled current sources for providing modulation pulses of a specified and known amperage to or from the electrical terminals 58, or independently controlled voltage sources for providing modulation pulses of a specified and known voltage at the electrical terminals 58 or to multiplexed current or voltage sources that are then connected to the electrical terminals 58. The operation of this modulation output circuitry 50, including alternative embodiments of suitable output circuitry for performing the same function of generating modulation pulses of a prescribed amplitude and width, is described more fully in U.S. Pat. Nos. 6,516,227 and 6,993,384, which are expressly incorporated herein by reference. Thus, it can be appreciated that the modulation output circuitry 50 is capable of delivering electrical energy to the electrodes 26 via the electrical terminals 58 at a series of incrementally increasing amplitude values when the calibration process is initiated, and for the purpose of evoking CAPs in the neural tissue in response to the series of incrementally increasing amplitude values and/or for delivering sub-threshold modulation therapy based on the perception threshold determined through the process of calibration.

The modulation output circuitry 50 may either include independently controlled current sources for providing stimulation pulses of a specified and known amperage to or from the electrical terminals 58, or independently controlled voltage sources for providing stimulation pulses of a specified and known voltage at the electrical terminals 58 or to multiplexed current or voltage sources that are then connected to the electrical terminals 58. The operation of this modulation output circuitry 50, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

Thus, it can be appreciated that the modulation output circuitry 50 is capable of delivering electrical energy to the electrodes 26 via the electrical terminals 58 for the purpose of providing therapy to the patient and/or evoking CAPs in the neural tissue during the calibration process described above.

The IPG 14 also includes monitoring circuitry 60 for monitoring the status of various nodes or other points 62 throughout the IPG 14, e.g., power supply voltages, temperature, battery voltage, and the like. Notably, the electrodes 26 fit snugly within the epidural space of the spinal column, and because the tissue is conductive, electrical measurements can be taken from the electrodes 26 in order to determine the coupling efficiency between the respective electrode 26 and the tissue and/or to facilitate fault detection with respect to the connection between the electrodes 26 and the modulation output circuitry 60 of the IPG 14.

More significant to the present inventions, the monitoring circuitry 60 is configured to measure characteristic(s) of the CAPs evoked in response to the stimulation of neural tissue via the modulation output circuitry 50 during the calibration process. The evoked potential measurement technique may be performed by generating an electrical field at one of the electrodes 26, which is strong enough to depolarize the neurons adjacent the stimulating electrode beyond a threshold level, thereby inducing the firing of an eCAP that propagates along the neural fibers. Such stimulation is preferably supra-threshold, but not uncomfortable. A suitable stimulation pulse for this purpose is, for example, 4 mA for 200 µs. While a selected one of the electrodes 26 is activated to generate the electrical field, a selected one or ones of the electrodes 26 (different from the activated electrode) is operated to record a measurable deviation in the voltage caused by the evoked potential due to the stimulation pulse at the stimulating electrode. To the extent that other physiological information is acquired for the purpose of triggering the modulation parameter adjustment process, the monitoring circuitry 60 may be coupled to various sensors. If the physiological measurements are electrical, the sensors may be one or more of the electrodes 26. For other types of non-electrical physiological information, however, separate sensors may be used for appropriate measurements.

The IPG 14 further includes a control/processing circuitry in the form of a microcontroller (µC) 64 (or a processor) that controls the control logic 52 over data bus 66, and obtains status data from the monitoring circuitry 60 via data bus 68. The IPG 14 additionally controls the timer logic 56. The IPG 14 further includes memory 70 and oscillator and clock circuit 72 coupled to the microcontroller 64.

Further, the microcontroller 64 generates the necessary control and status signals, which allow the microcontroller 64 to control the operation of the IPG 14 in accordance with a selected operating program and modulation parameters. In controlling the operation of the IPG 14, the microcontroller 64 is able to individually generate electrical energy at the electrodes 26 using the modulation output circuitry 50, in combination with the control logic 52 and timer logic 56, thereby allowing each electrode 26 to be paired or grouped with other electrodes 26, including the monopolar case electrode, to control the polarity, pulse amplitude, pulse rate, pulse width, and pulse duty cycle through which the electrical energy is provided. Further, the microcontroller 64 initiates the calibration process in response to the event.

The microcontroller 64 is also configured for initiating and performing the calibration process, including directing the modulation output circuitry 50 to deliver the electrical energy at increasing amplitude levels, directing the monitoring circuitry 60 to sense any eCAPs in response to the delivered electrical energy, determining the perception threshold of the patient in response to the sensing of the eCAPs, and computing a decreased amplitude suitable for sub-threshold modulation therapy based on the perception threshold.

The memory 70 may store various data (e.g. modulation parameters, reference eCAPs, threshold values, etc.) and a series of instructions to be executed by the microcontroller 64. The microcontroller 64, in combination with the memory 70 and oscillator and clock circuit 72, thus include a microprocessor system that carries out a program function in accordance with a suitable program stored in the memory 70. Alternatively, for some applications, the control/processing functions may be carried out by a suitable state machine.

The IPG 14 further includes an alternating current (AC) receiving coil 74 for receiving programming data (e.g., the operating program and/or modulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further includes a back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current modulation parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

Notably, if the RC 16, or alternatively the CP 18, is used to perform the automated modulation parameter adjustment technique, the measured eCAPs can be transmitted from the IPG 14 to the RC 16 or CP 18 via the back telemetry circuitry 78 and coil 80. The RC 16 or the CP 18 may perform the necessary routine to adjust the modulation parameters and transmit the adjusted set of modulation parameters to the IPG 14 so that the IPG 14 can generate the electrical modulation energy in accordance with the adjusted set of modulation parameters.

The IPG 14 further includes a rechargeable power source 82 and power circuits 84 for providing the operating power to the IPG 14. The rechargeable power source 82 may, e.g., include a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. Pat. No. 7,539,538, entitled "Low Power Loss Current Digital-to-Analog Converter Used in an Implantable Pulse Generator," which are expressly incorporated herein by reference. It should be noted that rather than the IPG 14, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
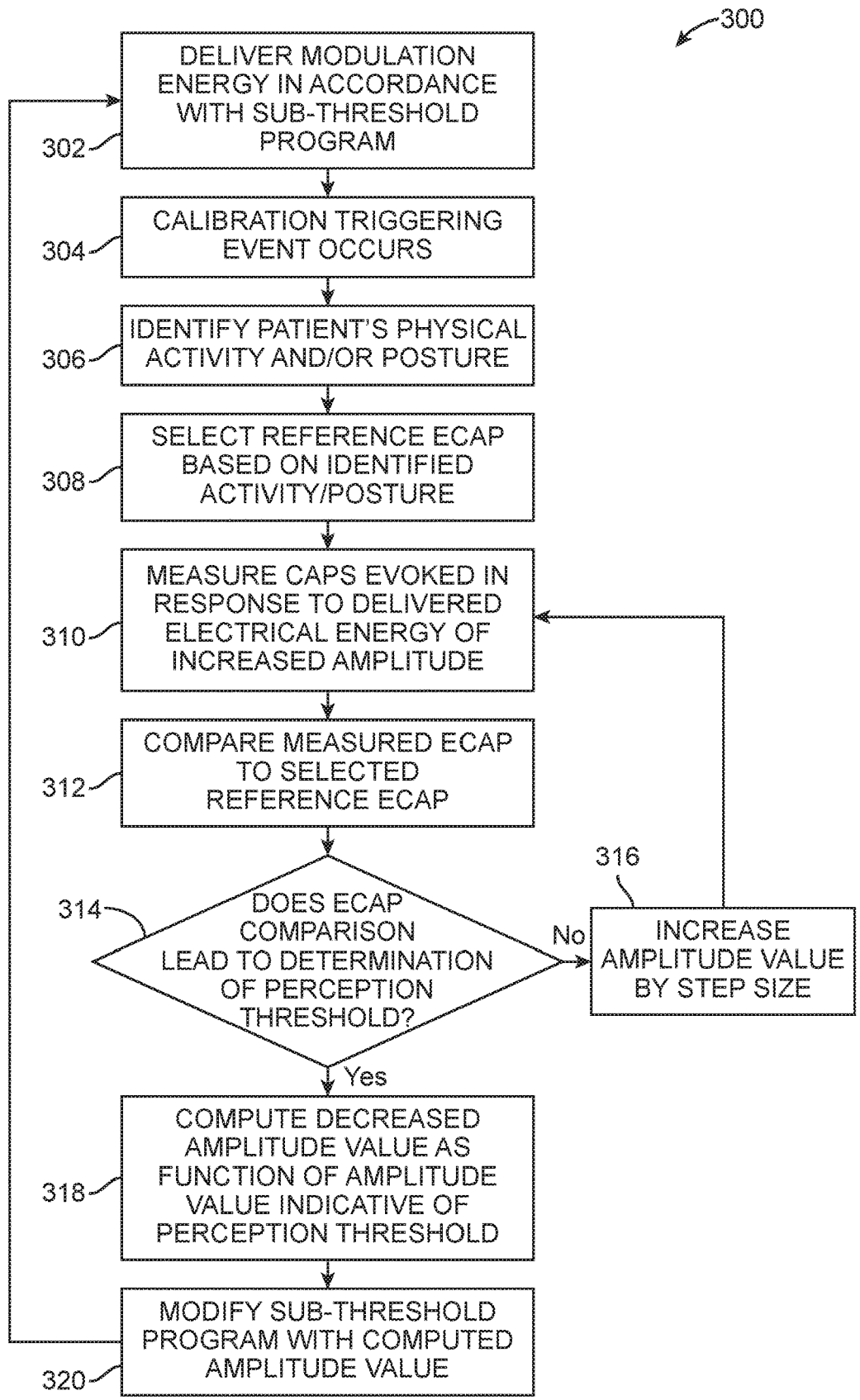
FIG. 5 is a flow diagram illustrating one method performed by the IPG of FIG. 2 to compute a suitable amplitude for sub-threshold modulation therapy.

Turning now to FIG. 5 an exemplary method 300 of using eCAPs to automatically compute a decreased amplitude suitable for sub-threshold modulation therapy will be described. First, the SCM system 10 delivers electrical modulation energy to a target tissue of the patient in accordance with the sub-threshold modulation program stored within the SCM system 10, thereby providing therapy to the patient without the perception of paresthesia (step 302). Next, a calibration triggering event occurs (step 304). As previously discussed, such triggering event can be an identified triggering physical activity and/or posture, a user-initiated signal, a signal indicating electrode-migration or a predetermined periodically recurring signal. Next, the SCM system 10 identifies the patient's physical activity and/or posture if it has not already been identified as a triggering event (step 306). Based on the patient/s physical activity and/or posture, the SCM system 10 selects, from the stored list of reference eCAPs, the reference eCAP corresponding to the identified physical activity and/or posture (step 308).

Next, the SCM system 10 delivers an electrical pulse train of a specified amplitude (which may initially be the programmed amplitude at which the electrical pulse train was delivered to provide the sub-threshold therapy), in response to which eCAP measurements are made for at least one pulse of the delivered electrical pulse train (step 310). To increase the signal-to-noise ratio, an eCAP measurement may be made after each pulse. Next, the SCM system 10 compares the eCAP measurement(s) to the selected reference eCAP corresponding to the identified physical activity and/or posture (step 312). As previously discussed, a characteristic (e.g., amplitude, peak delay, width, morphology) of an eCAP measurement or function of multiple eCAP measurements may be compared to the same characteristic of the reference eCAP.

If the eCAP comparison reveals that the perception threshold of the patient has not been reached (step 314), the SCM system 10 increases the amplitude of the delivered electrical energy by a step size (step 316), and returns to making eCAP measurement(s) in response to the delivered electrical energy at the increased amplitude (step 310). If the eCAP comparison reveals that the perception threshold of the patient has been reached (step 314), the SCM system 10 computes a decreased amplitude value as a function of the amplitude value indicative of the perception threshold (step 318). As described above, such function can be, e.g., a percentage of the determined perception threshold or a difference between the determined perception threshold and a constant. The SCM system 10 then modifies the sub-threshold modulation program with the computed amplitude value (step 320) and returns to step 302 to direct the IPG 14 to deliver electrical modulation energy in accordance with a modified sub-threshold modulation program, thereby providing therapy to the patient without the perception of paresthesia.

Thus, it can be appreciated that the sub-threshold calibration technique ensures that any intended sub-threshold therapy remains within an efficacious and energy efficient therapeutic window that may otherwise fall outside of this window due to environmental changes, such as lead migration or changes in patient's physical activity and/or posture. Although the sub-threshold calibration technique has been described with respect to sub-threshold therapy designed to treat chronic pain, it should be appreciated that this calibration technique can be utilized to calibrate any sub-threshold therapy provided to treat a patient with any disorder where the perception of paresthesia may be indicative of efficacious treatment of the disorder. Furthermore, although the sub-threshold calibration technique has been described as being performed in the IPG 14, it should be appreciated that this technique could be performed in the CP 18, or even the RC 16.

It should also be appreciated that although the sub-threshold calibration technique has been described with the adjustment of the amplitude of the electrical modulation energy, it should be appreciated that other modulation parameters that affect the intensity of the electrical modulation energy can be varied. For example, instead of incrementally increasing amplitude values relative to a programmed amplitude value while maintaining the pulse width value and pulse rate value the same, and computing a decreased amplitude value as a function of one of the increased amplitude values, pulse width values may be incrementally increased relative to a programmed pulse width value while maintaining the amplitude value and pulse rate value the same, and computing a decreased pulse width value as a function of one of the increased pulse width value. The significance is that a parameter that directly effects the intensity of the electrical modulation energy in a controllable and predictable fashion is used to calibrate the sub-threshold therapy.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method, comprising:
    providing a sub-perception therapy to a patient such that the patient does not perceive stimulation, wherein providing the sub-perception therapy includes initiating the sub-perception therapy and delivering the sub-perception therapy over a time period after the sub-perception therapy is initiated, and wherein providing the sub-perception therapy includes delivering electrical modulation energy to a target tissue site of the patient at a programmed intensity value;
    automatically determining occurrences of an event during the time period after initiating the sub-perception therapy;
    automatically responding to each of the occurrences of the event by performing an automatic calibration process for the sub-perception therapy to update the programmed intensity value accounting for environmental changes during the time period after initiating the sub-perception therapy, wherein the automatic calibration process that is automatically performed in response to each of the occurrences of the event during the time period includes automatically calibrating the sub-perception therapy to a perception threshold in response to each of the occurrences of the event, wherein the automatically calibrating the sub-perception therapy to the perception threshold includes:
        automatically detecting the perception threshold by delivering electrical modulation energy using a series of incrementally increasing intensity values relative to the programmed intensity value to increase an intensity of the delivered electrical modulation energy to at least the perception threshold, and sensing at least one evoked compound action potential (eCAP) indicative of the perception threshold in a population of neurons at the target tissue site of the patient in response to the delivery of the electrical modulation energy at the series of incrementally increasing intensity values;
        determining a corresponding intensity value from the series of incrementally increased intensity values for the at least one sensed eCAP indicative of the perception threshold;
        determining a decreased intensity value based on the corresponding intensity value; and
        updating the programmed intensity value for the electrical modulation energy using the decreased intensity value;
    continuing to deliver the sub-perception therapy during the time period by delivering electrical modulation energy to the target tissue site of the patient using the updated programmed intensity value.

2. The method of claim 1, wherein the determining the decreased intensity value based on the corresponding intensity value includes determining a percentage of the corresponding intensity value.

3. The method of claim 1, wherein the programmed intensity value is a programmed amplitude value, and the incrementally increasing intensity values are incrementally increasing amplitude values.

4. The method of claim 1, wherein the programmed intensity value is a programmed pulse width value, and the incrementally increasing intensity values are incrementally increasing pulse width values.

5. The method of claim 1, wherein the corresponding intensity value corresponds to the intensity value of the delivered electrical modulation energy in response to which a first one of the at least one eCAP is sensed.

6. The method of claim 1, further comprising:
    comparing a characteristic of each of the at least one sensed eCAP to a corresponding characteristic of a reference eCAP indicative of a perception threshold; and
    determining one of the corresponding intensity values based on the comparison.

7. The method of claim 6, wherein the characteristic of the each sensed eCAP includes amplitude.

8. The method of claim 6, wherein the characteristic of the each sensed eCAP includes at least one of peak delay, width, or waveform morphology.

9. The method of claim 6, wherein the at least one sensed eCAP comprises two or more eCAPs respectively sensed in response to the delivery of the electrical modulation energy at two or more of the intensity values, the method further comprising determining one of the two or more sensed eCAPs having the characteristic that best matches the characteristic of the reference eCAP, wherein selecting one of the series of incrementally increased intensity values includes selecting the intensity value that corresponds to the eCAP determined to best match the reference eCAP.

10. The method of claim 6, wherein the characteristic of the reference eCAP is a threshold value, the at least one sensed eCAP comprises one or more eCAPs respectively sensed in response to the delivery of the electrical modulation energy at each of two or more of the intensity values, the method further comprising determining a function of the one or more sensed eCAPs having the characteristic that equals or exceeds the threshold value.

11. The method of claim 6, further comprising:
identifying a physical activity and/or posture in which the patient is currently engaged; and
selecting, from a list of reference eCAP characteristics indicative of a perception threshold when the patient is engaged in a particular physical activity and/or posture, the reference eCAP characteristic corresponding to the identified physical activity and/or posture.

12. The method of claim 1, wherein the event is one of an identified physical activity and/or posture, a user-initiated signal, a signal indicating migration of an electrode from which the electrical modulation energy is delivered, and a predetermined periodically recurring signal.

13. The method of claim 1, wherein the determined decreased intensity value is reduced by a constant from the corresponding intensity value for the at least one sensed eCAP indicative of the perception threshold.

14. The method of claim 1, wherein both the electrical modulation energy delivered at the programmed intensity and the electrical energy delivered at the series of incrementally increasing intensity values comprise electrical pulse trains having a pulse intensity value.

15. A non-transitory machine-readable medium including instructions, which when executed by a machine, cause the machine to perform a method comprising:
providing a sub-perception therapy to a patient such that the patient does not perceive stimulation, wherein providing the sub-perception therapy includes initiating the sub-perception therapy and delivering the sub-perception therapy over a time period after the sub-perception therapy is initiated, and wherein providing the sub-perception therapy includes delivering electrical modulation energy to a target tissue site of the patient at a programmed intensity value;
automatically determining occurrences of an event during the time period after initiating the sub-perception therapy;
automatically responding to each of the occurrences of the event by performing an automatic calibration process for the sub-perception therapy to update the programmed intensity value accounting for environmental changes during the time period after initiating the sub-perception therapy, wherein the automatic calibration process that is automatically performed in response to each of the occurrences of the event during the time period includes automatically calibrating the sub-perception therapy to a perception threshold in response to each of the occurrences of the event, wherein the automatically calibrating the sub-perception therapy to the perception threshold includes:
automatically detecting the perception threshold by delivering electrical modulation energy using a series of incrementally increasing intensity values relative to the programmed intensity value to increase an intensity of the delivered electrical modulation energy to at least the perception threshold, and sensing at least one evoked compound action potential (eCAP) indicative of the perception threshold in a population of neurons at the target tissue site of the patient in response to the delivery of the electrical modulation energy at the series of incrementally increasing intensity values;
determining a corresponding intensity value from the series of incrementally increased intensity values for the at least one sensed eCAP indicative of the perception threshold;
determining a decreased intensity value based on the corresponding intensity value; and
updating the programmed intensity value for the electrical modulation energy using the decreased intensity value;
continuing to deliver the sub-perception therapy during the time period by delivering electrical modulation energy to the target tissue site of the patient using the updated programmed intensity value.

16. The non-transitory machine-readable medium of claim 15, wherein the determining the decreased intensity value based on the corresponding intensity value includes determining a percentage of the corresponding intensity value.

17. The non-transitory machine-readable medium of claim 15, wherein the method further comprises:
comparing a characteristic of each of the at least one sensed eCAP to a corresponding characteristic of a reference eCAP indicative of a perception threshold; and
determining one of the corresponding intensity values based on the comparison.

18. The non-transitory machine-readable medium of claim 17, wherein the characteristic of the each sensed eCAP includes at least one of amplitude, peak delay, width, or waveform morphology.

19. A neurostimulation system, comprising:
a neurostimulator configured to provide a sub-perception therapy to a patient such that the patient does not perceive stimulation, wherein the sub-perception therapy is provided by initiating the sub-perception therapy and delivering the sub-perception therapy over a time period after the sub-perception therapy is initiated, and wherein the sub-perception therapy is provided by delivering electrical modulation energy to a target tissue site of the patient at a programmed intensity value;
an event detector configured to automatically determine occurrences of an event during the time period after initiating the sub-perception therapy;
a sensor configured to sense evoked compound action potentials (eCAPs) in a population of neurons at the target tissue site in response to the delivery of the electrical modulation energy; and
a controller operably connected to the neurostimulator, the event detector and the sensor to automatically respond to each of the occurrences of the event by performing an automatic calibration process for the sub-perception therapy to update the programmed intensity value accounting for environmental changes during the time period after initiating the sub-perception therapy, wherein the automatic calibration process that is automatically performed in response to each of the occurrences of the event during the time period includes automatically calibrating the sub-perception therapy to a perception threshold in response to each of the occurrences of the event, wherein the automatically calibrating the sub-perception therapy to the perception threshold includes:

automatically detecting the perception threshold, by delivering electrical modulation energy using a series of incrementally increasing intensity values relative to the programmed intensity value to increase an intensity of the delivered electrical modulation energy to at least the perception threshold, and sensing at least one evoked compound action potential (eCAP) indicative of the perception threshold in a population of neurons at the target tissue site of the patient in response to the delivery of the electrical modulation energy at the series of incrementally increasing intensity values;

determining a corresponding intensity value from the series of incrementally increased intensity values for the at least one sensed eCAP indicative of the perception threshold;

determining a decreased intensity value based on the corresponding intensity value; and updating the programmed intensity value for the electrical modulation energy using the decreased intensity value;

wherein the controller is configured to control the neurostimulator to continue to deliver the sub-perception therapy during the time period by delivering electrical modulation energy to the target tissue site of the patient using the updated programmed intensity value.

20. The system of claim 19, wherein the event is one of an identified physical activity and/or posture, a user-initiated signal, a signal indicating migration of an electrode from which the electrical modulation energy is delivered, and a predetermined periodically recurring signal.

* * * * *